US00PP18360P2

(12) United States Plant Patent
Klemm

(10) Patent No.: US PP18,360 P2
(45) Date of Patent: Dec. 25, 2007

(54) ***NEMESIA* PLANT NAMED 'KLENE04146'**

(50) Latin Name: ***Nemesia* hybrid**
Varietal Denomination: KLENE04146

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/343,865

(22) Filed: Jan. 31, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

UPOV–ROM Gtitm, Plant Variety Database, 2006/04, GTI Jouve Retrieval Software, Citation for Nemesia 'Klene 04146' one page.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Nemesia* plant named 'KLENE04146', characterized by its upright to somewhat outwardly spreading plant habit; freely branching habit; dense and bushy appearance; numerous large violet-colored flowers; and good garden performance.

1 Drawing Sheet

Botanical designation: *Nemesia* hybrid.
Cultivar denomination: 'KLENE04146'.

BACKGROUND OF THE INVENTION

The present invention relates to a new and distinct cultivar of *Nemesia* plant, botanically known as *Nemesia* hybrid and referred to by the name 'KLENE04146'.

The new *Nemesia* is a product of a planned breeding program conducted by the Inventor in Stuttgart, Germany. The objective of the program is to create new upright and freely branching *Nemesia* cultivars with attractive flowers and good garden performance.

The new *Nemesia* originated from an open-pollination of the *Nemesia* hybrid cultivar Ravello, not patented, as the female, or seed, parent with an unidentified *Nemesia* hybrid selection during the summer of 2002. The cultivar KLENE04146 was discovered and selected by the Inventor as a flowering plant within the progeny of the stated open-pollination in a controlled environment in Stuttgart, Germany in May, 2003.

Asexual reproduction of the new *Nemesia* by terminal cuttings in a controlled environment in Stuttgart, Germany since May, 2003, has shown that the unique features of this new *Nemesia* are stable and are reproduced true to type in successive generations.

SUMMARY OF THE INVENTION

The new *Nemesia* has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'KLENE04146' and distinguish 'KLENE04146' as a new and distinct cultivar:

1. Upright to somewhat outwardly spreading plant habit.
2. Freely branching habit; dense and bushy appearance.
3. Numerous large violet-colored flowers.
4. Good garden performance.

Plants of the new *Nemesia* differ primarily from plants of the female parent selection in plant shape as plants of the new *Nemesia* are more outwardly spreading than plants of the female parent selection.

Plants of the new *Nemesia* can be compared to plants of the cultivar Nemo Blue, not patented. In side-by-side comparisons conducted in Stuttgart, Germany, plants of the new *Nemesia* differed primarily from plants of the cultivar Nemo Blue in the following characteristics:

1. Plants of the new *Nemesia* were larger than plants of the cultivar Nemo Blue.
2. Plants of the new *Nemesia* were more freely branching than plants of the cultivar Nemo Blue.
3. Plants of the new *Nemesia* were more freely flowering than plants of the cultivar Nemo Blue.

BRIEF DESCRIPTION OF THE PHOTOGRAPH

The accompanying colored photograph illustrates the overall appearance of the new *Nemesia,* showing the colors as true as it is reasonably possible to obtain in colored reproductions of this type. Colors in the photograph may differ slightly from the color values cited in the detailed botanical description which accurately describe the colors of the new *Nemesia.* The photograph comprises a side perspective view of a typical plant of 'KLENE04146' grown in a container.

DETAILED BOTANICAL DESCRIPTION

The aforementioned photograph and following observations and averaged measurements describe plants grown in Stuttgart, Germany, in an outdoor nursery during the summer with day temperatures ranging from 20° C. to 35° C. and night temperatures ranging from 10° C. to 20° C. Plants were pinched two times. Plants were about 6.5 months old when the photograph and description were taken. Color references are made to The Royal Horticultural Society Colour Chart, 1995 Edition, except where general terms of ordinary dictionary significance are used.

Botanical classification: *Nemesia* hybrid cultivar KLENE04146.

Parentage:

*Female parent.*—*Nemesia* hybrid cultivar Ravello, not patented.

*Male parent.*—Unidentified *Nemesia* hybrid selection, not patented.

Propagation:

*Type.*—By vegetative cuttings.

*Time to initiate roots, summer.*—About 6 days at 25° C.

*Time to initiate roots, winter.*—About 10 days at 25° C.

*Time to develop roots, summer.*—About 14 days at 25° C.

*Time to develop roots, winter.*—About 17 days at 25° C.

*Root description.*—Fine; white in color.

*Rooting habit.*—Freely branching.

Plant description:

*General appearance.*—Upright to somewhat outwardly spreading plant habit; inverted triangle. Freely branching, typically about 50 lateral branches per plant. Moderately vigorous growth habit.

*Plant height.*—About 20 cm to 25 cm.

*Plant diameter or spread.*—About 20 cm to 30 cm.

*Lateral branches.*—Length: About 25 cm to 30 cm. Diameter: About 5 mm. Internode length: About 2.5 cm to 4 cm. Strength: Strong. Texture: Smooth, glabrous. Color: Close to 146A.

*Foliage description.*—Arrangement: Opposite, simple; sessile. Shape: Ovate. Apex: Acute. Base: Obtuse. Length: About 2 cm to 4 cm. Width: About 7 mm to 15 mm. Margin: Serrate. Texture, upper and lower surfaces: Smooth, glabrous; leathery. Venation pattern: Pinnate. Color: Developing leaves, upper surface: 147A. Developing leaves, lower surface: 147B. Fully expanded leaves, upper surface: 147B. Fully expanded leaves, lower surface: 147C. Venation, upper surface: 146C. Venation, lower surface: 146D.

Flowering description:

*Arrangement/appearance.*—Zygomorphic solitary flowers arranged on terminal racemes; flowering acropetally towards apex. Flowers face upright and outward. Flowers last about ten days on the plant. Flowers not persistent.

*Natural flowering season.*—Flowering continuous from the spring through the summer in Germany.

*Quantity of flowers.*—Freely flowering with about 25 to 30 flowers per lateral branch.

*Fragrance.*—None detected.

*Inflorescence length.*—About 1.5 cm.

*Inflorescence diameter.*—About 4 cm to 5 cm.

*Flower diameter.*—About 2.5 cm.

*Flower depth.*—About 1 cm to 1.5 cm.

*Flower buds.*—Shape: Rounded. Length: About 1 mm to 5 mm. Diameter: About 3 mm. Color: Close to 146A.

*Petals.*—Arrangement/shape: Four upper petals are fused at base to form an upright lobed and arched banner lip; lower petal modified into a larger lip with nectar spur and central protuberance which serves as pollinator nectar guide and landing platform; petals, obovate. Apex: Rounded. Margin: Entire. Length: Upper petals: About 1 cm. Lower petal: About 1.2 cm. Width: Upper petals: About 5 mm. Lower petal: About 2.2 cm. Texture, upper and lower surfaces: Smooth, glabrous; velvety. Color: When opening and fully opened, upper surface: 86A; color becoming closer to 86B with development. When opening and fully opened, lower surface: 86D. Nectar guide: Close to 4A. Nectar spur, when opening: Close to 1C. Nectar spur, fully opened: Close to 2D.

*Sepals.*—Quantity: Five-parted, star-shaped calyx. Shape: Oblong. Apex: Acute. Base: Fused. Margin: Entire. Length: About 3 mm. Diameter: About 1 mm. Texture, upper and lower surfaces: Smooth, glabrous. Color, upper and lower surfaces: Close to 146A.

*Peduncle.*—Length: About 5 mm to 10 mm. Diameter: About 1 mm. Strength: Weak. Color: Close to 146A. Texture: Smooth, glabrous.

*Androecium.*—Stamen number: Four per flower. Anther shape: Reniform. Anther length: About 1 mm. Anther color: 10C. Amount of pollen: Moderate. Pollen color: 14A.

*Gynoecium.*—Pistil number: One per flower. Pistil length: About 1 mm. Style length: About 0.75 mm. Stigma color: 150D.

*Seeds.*—Length: About 1 mm. Diameter: About 0.5 mm. Color: Light brown.

Disease/pest resistance: Plants of the new *Nemesia* have not been observed to be resistant to pathogens or pests common to *Nemesias.*

Garden performance: Plants of the new *Nemesia* have good garden performance; plants of the new *Nemesia* have been observed to tolerate rain, wind and temperatures from about 0° C. to about 35° C.

It is claimed:

1. A new and distinct cultivar of *Nemesia* plant named 'KLENE04146', as illustrated and described.

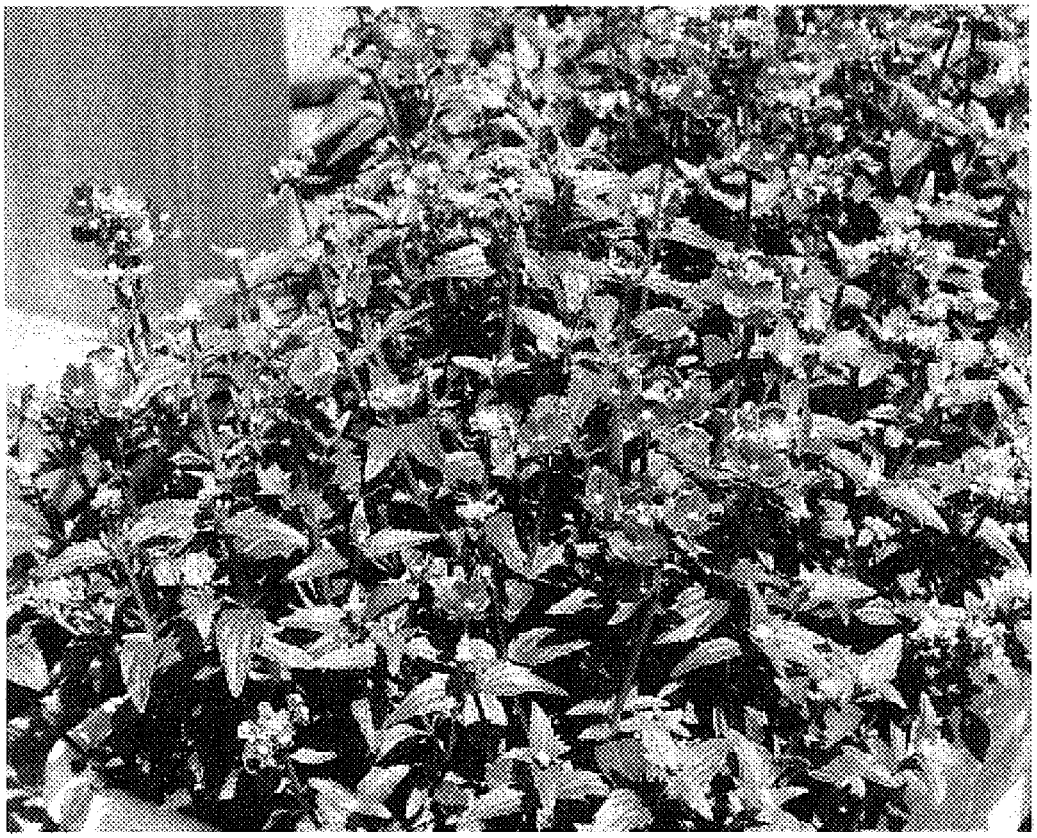

* * * * *